United States Patent
Bowlby et al.

(10) Patent No.: US 6,589,986 B2
(45) Date of Patent: Jul. 8, 2003

(54) METHODS OF TREATING ANXIETY DISORDERS

(75) Inventors: Mark R. Bowlby, Richboro, PA (US); Sharon Joy Rosenzweig-Lipson, East Brunswick, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/022,579

(22) Filed: Dec. 17, 2001

(65) Prior Publication Data

US 2002/0111379 A1 Aug. 15, 2002

Related U.S. Application Data

(60) Provisional application No. 60/256,834, filed on Dec. 20, 2000.

(51) Int. Cl.[7] .................. A01N 47/10; A01N 37/12; C07C 261/00
(52) U.S. Cl. .................. 514/484; 514/485; 514/535; 514/903; 560/27
(58) Field of Search ................. 514/485, 535, 514/903, 484; 560/27

(56) References Cited

U.S. PATENT DOCUMENTS

| | | | |
|---|---|---|---|
| 5,384,330 A | * | 1/1995 | Dieter et al. ............. 514/535 |
| 5,849,789 A | | 12/1998 | Rostock et al. |
| 5,852,053 A | | 12/1998 | Rostock et al. |
| 5,914,425 A | | 6/1999 | Meisel et al. |
| 6,117,900 A | | 9/2000 | Rundfeldt |
| 6,326,385 B1 | | 12/2001 | Wickenden et al. |
| 6,372,767 B1 | | 4/2002 | McNaughton-Smith et al. |
| 6,495,550 B2 | | 12/2002 | McNaughton-Smith et al. |
| 2001/0049444 A1 | | 12/2001 | McNaughton-Smith et al. |
| 2002/0013349 A1 | | 1/2002 | Wickenden et al. |
| 2002/0052393 A1 | | 5/2002 | McNaughton-Smith et al. |
| 2002/0091122 A1 | | 7/2002 | McNaughton-Smith et al. |

FOREIGN PATENT DOCUMENTS

| | | |
|---|---|---|
| WO | WO 01/01970 A2 | 1/2001 |
| WO | WO 01/10380 A2 | 2/2001 |

OTHER PUBLICATIONS

Chris Rundfeldt, Epilepsy Research, 35, 99–107 (1999).
Chris Rundfeldt, Neuroscience Letters, 282, 73–79 (2000).

* cited by examiner

*Primary Examiner*—Alan L. Rotman
*Assistant Examiner*—Hector M Reyes
(74) *Attorney, Agent, or Firm*—Kimberly R. Hild

(57) ABSTRACT

This invention provides methods for treating, preventing or inhibiting anxiety, anxiety-related conditions and phobias in a mammal using compounds of the formula:

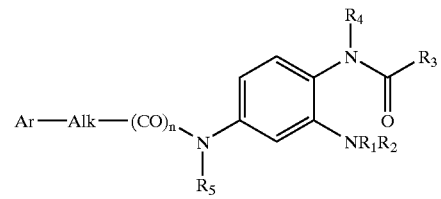

wherein: $R_1$ is H, alkyl, alkanoyl or the radical Ar; $R_2$ is H or alkyl; $R_3$ is alkoxy, $NH_2$, alkylamino, dialkylamino, amino substituted by the radical Ar, alkyl, alkenyl, alkynyl, or the radicals Ar or ArO—; $R_4$ is H, alkyl or the radical Ar; $R_5$ is H or alkyl or the radical Ar; or a pharmaceutically acceptable salt or ester form thereof; Ar is an optionally substituted phenyl radical; and n is 0 or 1, or a pharmaceutically acceptable salt or ester form thereof, with the methods particularly including the use of N-[2-amino-4-(4-fluorobenzylamino)-phenyl]carbamic acid ethyl ester, also known as retigabine.

7 Claims, No Drawings

METHODS OF TREATING ANXIETY DISORDERS

This application claims priority from copending provisional application Ser. No. 60/256,834, filed Dec. 20, 2000, the entire disclosure of which is hereby incorporated by reference.

This invention relates to novel methods for treating, preventing or inhibiting anxiety and anxiety-related conditions in a mammal, preferably in a human. The methods of this invention include the treatment, prevention, inhibition and amelioration of conditions including anxiety, generalized anxiety disorder, panic anxiety, obsessive compulsive disorder, social phobia, post-traumatic stress disorder, agoraphobia and specific phobias.

BACKGROUND OF THE INVENTION

U.S. Pat. No. 5,384,330 (Dieter et al.) teaches pharmacologically active 1,2,4-triaminobenzene derivatives of the General Formula:

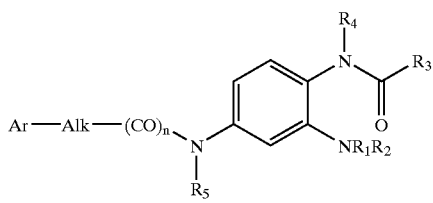

and their properties as anti-epileptic, muscle relaxing, fever-reducing and peripheral analgesic agents.

U.S. Pat. Nos. 5,849,789 and 5,852,053 (both to Rostock et al.) teaches the use of retigabine for the treatment of neurodegenerative disorders, including those associated with stroke.

U.S. Pat. No. 5,914,425 (Meisel et al.) teaches novel crystalline forms of retigabine.

U.S. Pat. No. 6,117,900 teaches the use of retigabine, also known as N-[2-amino-4-(4-fluorobenzylamino)-phenyl] carbamic acid ethyl ester, for the treatment of neuropathic pain.

DESCRIPTION OF THE INVENTION

This invention provides methods for treating anxiety disorders and anxiety-related conditions in a mammal, preferably including methods for such treatment in humans.

Among the compounds useful in the methods of this invention are those disclosed in U.S. Pat. No. 5,384,330 (Dieter et al.), the contents of which is incorporated herein by reference. The compounds include those of the formula:

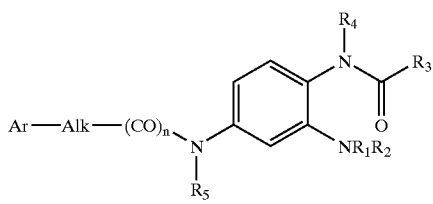

wherein:
- $R_1$ is selected from hydrogen, $C_1$–$C_6$-alkyl, $C_2$–$C_6$-alkanoyl or the radical Ar;
- $R_2$ is selected from hydrogen or $C_1$–$C_6$-alkyl;
- $R_3$ is selected from $C_1$–$C_6$-alkoxy, $NH_2$, $C_1$–$C_6$-alkylamino, $C_1$–$C_6$-dialkylamino, amino substituted by the radical Ar, $C_1$–$C_6$-alkyl, $C_2$–$C_6$-alkenyl, $C_2$–$C_6$-alkynyl, the radical Ar or the radical ArO—;
- $R_4$ is selected from hydrogen, $C_1$–$C_6$-alkyl or the radical Ar;
- $R_5$ is selected from hydrogen or $C_1$–$C_6$-alkyl or the radical Ar;
- Alk indicates a straight or branched alkylene group with 1-9 carbon atoms, which can also be substituted by the radical Ar;
- Ar is a phenyl radical substituted by the radicals $R_6$, $R_7$ and/or $R_8$ where these radicals $R_6$, $R_7$ and $R_8$ are the same or different and represent H, $C_1$–$C_6$-alkyl, $C_3$–$C_7$-cycloalkyl, hydroxy, $C_1$–$C_6$-alkoxy, $C_2$–$C_6$-alkanoyloxy, halogen, hydroxy, $C_1$–$C_6$-halogenoalkyl, —CN, —$NH_2$, —NH—$C_1$–$C_6$-alkyl, —N($C_1$–$C_6$-alkyl)$_2$, —$CO_2$H, —CO—$C_1$–$C_6$-alkyl, —CO—O—$C_1$–$C_6$-alkyl, —COAr, —CO—OAr, —$CONH_2$, —CONH—$C_1$–$C_6$-alkyl, —CON($C_1$–$C_6$-alkyl)$_2$, —CONHAr, —NH—CO—$C_1$–$C_6$-alkyl, —NHCO—Ar, —NHCO—$C_1$–$C_6$-alkoxy, —N—H—CO—Ar, —NHCO—$NH_2$, —NHCO—N(—$C_1$–$C_6$-alkyl)$_2$, —NHCO—NHAr, —NH—$SO_2$—C-1-$C_6$-alkyl, —NH—$SO_2$Ar, —NH—$SO_2$-nitrophenyl, —$SO_2$—OH, —$SO_2$—$C_1$–$C_6$-alkyl, —$SO_2$—Ar, —$SO_2$—$C_1$–$C_6$-alkoxy, —$SO_2$—OAr, —$SO_2$—$NH_2$, —$SO_2$—NH—$C_1$–$C_6$-alkyl, —$SO_2$—N($C_1$–$C_6$-alkyl)$_2$, —$SO_2$—NHAr, —$SO_2$—$C_1$–$C_6$-alkoxy;
- n is 0 or 1;

or a pharmaceutically acceptable salt thereof.

The alkyl groups, halogenalkyl groups, alkenyl groups, alkynyl groups, alkoxy groups, alkylamino groups, alkanoyl amino groups, alkanoyloxy groups and alkanoyl groups in general can be straight or branched. The same also applies to alkyl and alkyloxy groups (=alkoxy groups) if these are components of more complicated radicals for example in the form of a monoalkyl- or dialkylamino group, alkanoylamino group, carbalkoxy group, alkylcarbonyl group and analogous groups. The $C_3$–$C_7$-cycloalkyl group is preferably cyclopentyl or cyclohexyl. $C_2$–$C_6$-alkenyl preferably represents allyl. $C_2$–C6-alkynyl preferably represents propargyl.

The halogen atoms are chlorine, bromine or fluorine, in particular chlorine of fluorine. The alkyl and alkoxy groups as such or as components of groups of more complicated radicals consist in particular of 1–4 carbon atoms, preferably 1 or 2 carbon atoms. Alkanoyl groups, such as alkanoylamino groups or alkanoyloxy groups consist in particular of 2–4, preferably 2–3 carbon atoms. Alk consists in particular of 1–3, preferably 1 or 2 carbon atoms.

Among the more preferred compounds of this group are:

2-Amino-4-(4-fluorobenzylamino)-1-ethoxycarbonylaminobenzene;

2-Amino-4-(4-trifluoromethylbenzylamino)-1-ethoxycarbonylamino-benzene;

2-Amino-4-benzylamino-1-ethoxycarbonylamino-benzene;

2-Amino-4-(3,5-dichlorobenzylamino)-1-ethoxycarbonylamino benzene;

2-Amino-4-(3,5-dichlorobenzylamino)-1-propyloxycarbonylamino benzene;

2-Amino-(2-chlorobenzylamino)-1-(diethylcarbamoylamino) benzene;

2-Amino-4-(2,4-dichlorobenzylamino)-1-(dimethylcarbamoylamino) benzene; and 1,2-Diacetylamino-4-(4-fluorobenzylamino) benzene; each of which can be prepared as described in U.S. Pat. No. 5,384,330.

Among the most preferred compounds for use in the methods of this invention are N-[2-amino-4-(4-fluorobenzylamino)-phenyl]carbamic acid and its pharmaceutically acceptable salts and ester forms. Of particular preference is retigabine, also known as N-[2-amino-4-(4-fluorobenzylamino)-phenyl]carbamic acid ethyl ester (CAS Registry No. 150812-12-7), having the formula:

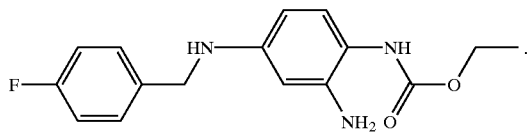

Also useful in the methods of this invention are the metabolite forms of retigabine which may be isolated from blood, urine or feces of recipients of N-[2-amino-4-(4-fluorobenzylamino)-phenyl]carbamic acid ethyl ester. The metabolites include the glucoside of retigabine, [4-(4-Fluoro-benzylamino)-2-(3,4,5-trihydroxy-6-hydroxymethyl-tetrahydropyran-2-ylamino)-phenyl]-carbamic acid ethyl ester, as well as its two glucoronide analogs, 6-[2-Ethoxycarbonylamino-5-(4-fluoro-benzylamino)-phenylamino]-3,4,5-trihydroxy-tetrahydro-pyran-2-carboxylic acid and 6-[(3-Amino-4-ethoxycarbonylamino-phenyl)-(4-fluoro-benzyl)-amino]-3,4,5-trihydroxy-tetrahydro-pyran-2-carboxylic acid. Further metabolites include N-[2-Amino-4-(4-fluoro-benzylamino)-phenyl]acetamide, its cyclized analog (4-Fluoro-benzyl)-2-methyl-1H-benzoimidazol-5-yl)amine and the glucoronide analogs of N-[2-Amino-4-(4-fluoro-benzylamino)-phenyl] acetamide, 6-[(4-Acetylamino-3-amino-phenyl)-(4-fluoro-benzyl)-amino]-3,4,5-trihydroxy-tetrahydro-pyran-2-carboxylic acid and 6-[2-Acetylamino-5-(4-fluoro-benzylamino)-phenylamino]-3,4,5-trihydroxy-tetrahydro-pyran-2-carboxylic acid.

The applications may utilize conventional oral, rectal, parenteral or intravenous delivery methods as conventionally utilized in medical or veterinary practice. Most preferable in most instance for home use are oral tablets or capsules or neat compound or powdered or granular pharmaceutical formulations which may be mixed with chewable or liquid formulations or food materials or liquids acceptable to the recipient.

The methods of this invention include the treatment, prevention, inhibition and amelioration of conditions in mammals in need thereof including anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias. Such mammals may be those presently experiencing the anxiety-related symptoms or conditions of these disorders or those subject to such occurrences. Specific anxiety related phobias which may be treated with these methods are those commonly experienced in clinical practice including, but not limited to, fear of animals, insects, storms, driving, flying, heights or crossing bridges, closed or narrow spaces, water; blood or injury, as well as extreme fear of inoculations or other invasive medical or dental procedures.

The methods for treating, preventing, inhibiting or ameliorating the maladies listed above or their symptoms comprise administering to a mammal in need thereof a pharmaceutically effective amount of a compound of this invention. A particular method of treating, preventing, inhibiting or ameliorating the maladies in question comprises administering to the mammal in need of such assistance a pharmaceutically or therapeutically effective amount of N-[2-amino-4-(4-fluorobenzylamino)-phenyl]carbamic acid or a pharmaceutically acceptable salt or ester form thereof. Particularly included in these methods is the use of N-[2-amino-4-(4-fluorobenzylamino)-phenyl]carbamic acid ethyl ester, also known as retigabine, or a pharmaceutically acceptable salt form thereof.

As used herein, the terms "pharmaceutically effective amount" or "therapeutically effective amount" mean the total amount of each active component of the pharmaceutical composition or method that is sufficient to show a meaningful patient benefit, i.e., treatment, prevention, amelioration, or a decrease in the frequency of the anxiety or anxiety-related condition or symptoms in question. When applied to an individual active ingredient, administered alone, the term refers to that ingredient alone. When applied to a combination, the term refers to combined amounts of the active ingredients that result in the therapeutic effect, whether administered in combination, serially or simultaneously.

The methods of this invention may be accomplished with a daily dose of the active compounds described above of from about 0.1 mg/kg to about 30 mg/kg. Doses may be administered as a single regimen or as a continuous regimen divided by two or more doses over the course of a day.

Human administration may be at dosages of from about 10 mg BID to about 1000 mg BID, preferably from about 50 mg BID to about 500 mg BID, more preferably at a dose of from about 100 mg BID to about 300 mg BID.

Compounds as described in U.S. Pat. No. 5,384,330, including retigabine, can be administered orally using conventional pharmaceutical excipients or carriers, preferably coated or contained in hard or soft gelatin capsules. Examples of oral formulations contained in hard gelatin capsules can include those in which the active compound comprises from about 45% to 50%, by weight, of the formulation. Microcrystalline cellulose comprises from about 43% to about 47%, povidone comprises from about 3% to about 4%, and silicon dioxide and magnesium stearate each comprise from about 0.3% to about 0.7%, each by weight. Specific examples of capsules containing 50 mg, 100 mg and 200 mg may be formulated utilizing the following lists of components.

| Ingredient | Amount/Capsule |
| --- | --- |
| 50 mg Retigabine Capsules | |
| Retigabine | 50.0 mg |
| Microcrystalline Cellulose, NF | 45.5 mg |
| Povidone, USP | 3.5 mg |
| Silicon Dioxide, Colloidal, anhydrous, NF | 0.5 mg |
| Magnesium Stearate, EP | 0.5 mg |
| Theoretical Fill Weight | 100 mg |
| 100 mg Retigabine Capsules | |
| Retigabine | 100.0 mg |
| Microcrystalline Cellulose, NF | 91.0 mg |
| Povidone, USP | 7.0 mg |
| Silicon Dioxide, Colloidal, anhydrous, NF | 1.0 mg |
| Magnesium Stearate, EP | 1.0 mg |
| Theoretical Fill Weight | 200 mg |
| 200 mg Retigabine Capsules | |
| Retigabine | 200.0 mg |
| Microcrystalline Cellulose, NF | 182.0 mg |
| Povidone, USP | 14.0 mg |
| Silicon Dioxide, Colloidal, anhydrous, NF | 2.0 mg |

-continued

| Ingredient | Amount/Capsule |
|---|---|
| Magnesium Stearate, EP | 2.0 mg |
| Theoretical Fill Weight | 400 mg |

The ingredients in the formulations above can be prepared using the following steps.

1) Weigh separately the active ingredient (retigabine), preferably screened through an 800 micron screen, and the microcrystalline cellulose components.
2) Prepare a granulation solution by dissolving the Povidone, USP in purified water.
3) Place the ingredients from Step 1 into a suitable blender and mix thoroughly.
4) Screen the mixture from Step 3 through a 1000 μm screen and place the screened mixture into the vessel of a fluidized bed granulator.
5) Heat the ingredients in the fluid bed granulator up to 27° C. product temperature while mixing.
6) Add the granulation solution from Step 2 to the fluid bed.
7) Dry the granulate in the fluid bed.
8) Weigh the colloidal silicon dioxide component, preferably screened through a 1000 μm screen, and the magnesium stearate component, preferably screened through a 600 μm screen.
9) Add the silicon dioxide and magnesium stearate components to the fluid bed granulator's vessel containing the dried granulate from Step 7 and mix the components thoroughly.
10) Screen the mixed components from Step 9, preferably through a 800 μm screen.
11) Transfer the final screened components into a suitable blender and mix thoroughly.

The final component mixture from Step 11 can then be coated, encapsulated or compressed into tablets utilizing conventional tablet excipients or carriers, as desired. It will be understood that oral dosage forms within the scope of this invention can be prepared using the components listed above in respective amounts according the dose of active ingredient in the particular formulation. For veterinary uses, the final mixture of Step 11 can be administered neat or mixed into foods acceptable to the animal in question. Further, the mixtures can be formulated into tablets, capsules or coated products, as described above, or integrated into conventional veterinary medicaments or food products.

For intravenous administration, the compounds described herein may be prepared and maintained in conventional lyophylized formulations and reconstituted prior to administration with an intravenously acceptable saline solution, such as a 0.9% saline solution. The pH of the intravenous formulation can be adjusted, as needed, with an intravenous and pharmaceutically acceptable acid, such as methanesulfonic acid.

What is claimed:

1. A method of treatment or inhibition of anxiety disorders in a mammal, the method comprising administering to a mammal in need thereof a pharmaceutically effective amount of a compound of the formula:

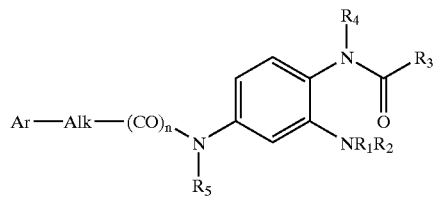

wherein:
$R_1$ is selected from hydrogen, $C_1$–$C_6$-alkyl, $C_2$–$C_6$-alkanoyl or the radical Ar;
$R_2$ is selected from hydrogen or $C_1$–$C_6$-alkyl;
$R_3$ is selected from $C_1$–$C_6$-alkoxy, $NH_2$, $C_1$–$C_6$-alkylamino, $C_1$–$C_6$-dialkylamino, amino substituted by the radical Ar, $C_1$–$C_6$-alkyl, $C_2$–$C_6$-alkenyl, $C_2$–$C_6$-alkynyl, the radical Ar or the radical ArO—;
$R_4$ is selected from hydrogen, $C_1$–$C_6$-alkyl or the radical Ar;
$R_5$ is selected from hydrogen or $C_1$–$C_6$-alkyl or the radical Ar;
Alk is a straight or branched alkylene group with 1–9 carbon atoms, which can also be substituted by the radical Ar;
Ar is a phenyl radical substituted by the radicals $R_6$, $R_7$ and/or $R_8$ where these radicals $R_6$, $R_7$ and $R_8$ are the same or different and represent $C_1$–$C_6$-alkyl, $C_3$–$C_7$-cycloalkyl, hydroxy, $C_1$–$C_6$-alkoxy, $C_2$–$C_6$-alkanoyloxy, halogen, hydroxy, $C_1$–$C_6$-halogenoalkyl, —CN, —$NH_2$, —NH—$C_1$–$C_6$-alkyl, —N($C_1$–$C_6$-alkyl)$_2$, —$CO_2H$, —CO—$C_1$–$C_6$-alkyl, —CO—O—$C_1$–$C_6$-alkyl, —COAr, —CO—OAr, —$CONH_2$, —CONH—$C_1$–$C_6$-alkyl —CON($C_1$–$C_6$-alkyl)$_2$, —CONHAr, —NH—CO—$C_1$–$C_6$-alkyl, —NHCO—Ar, —NHCO—$C_1$–$C_6$-alkoxy, —N—H—CO—Ar, —NHCO—$NH_2$, —NHCO—N(—$C_1$–$C_6$-alkyl)$_2$, —NHCO—NHAr, —NH—$SO_2$—C—1$C_6$-alkyl, —NH—$SO_2$Ar, —NH—$SO_2$-nitrophenyl, —$SO_2$—OH, —$SO_2$—$C_1$–$C_6$-alkyl, —$SO_2$—Ar, —$SO_2$—$C_1$–$C_6$-alkoxy, —$SO_2$—OAr, —$SO_2$—$NH_2$, —$SO_2$—NH—$C_1$–$C_6$-alkyl, —$SO_2$—N($C_1$–$C_6$-alkyl)$_2$, —$SO_2$—NHAr, or —$SO_2$—$C_1$–$C_6$-alkoxy; and
n is 0 or 1;
or a pharmaceutically acceptable salt thereof.

2. The method of claim 1 wherein the compound administered comprises at least one of:
2-Amino-4-(4-fluorobenzylamino)-1-ethoxycarbonylaminobenzene;
2-Amino-4-(4-trifluoromethylbenzylamino)-1-ethoxycarbonylamino-benzene;
2-Amino-4-benzylamino-1-ethoxycarbonylamino-benzene;
2-Amino-4-(3,5-dichlorobenzylamino)-1-ethoxycarbonylamino benzene;
2-Amino-4-(3,5-dichlorobenzylamino)-1-propyloxycarbonylamino benzene;
2-Amino-(2-chlorobenzylamino)-1-(diethylcarbamoylamino) benzene;
2-Amino-4-(2,4-dichlorobenzylamino)-1-(dimethylcarbamoylamino) benzene; or
1,2-Diacetylamino-4-(4-fluorobenzylamino) benzene;
or a pharmaceutically acceptable salt thereof.

3. The method of claim of claim 1 wherein the mammal is a human.

4. The method of claim 1 wherein the anxiety disorder is selected from the group of anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia or specific phobias.

5. A method of treatment or inhibition of anxiety disorders in a mammal, the method comprising administering to a mammal in need thereof a pharmacologically effective amount of N-[2-amino-4-(4-fluorobenzylamino)-phenyl] carbamic acid or a pharmaceutically acceptable salt or ester form thereof.

6. The method of claim 5 comprising administering to the mammal in need thereof a pharmacologically effective amount of N-[2-amino-4-(4-fluorobenzylamino)-phenyl] carbamic acid ethyl ester or a pharmaceutically acceptable salt form thereof.

7. The method of claim 5 wherein the anxiety disorder is selected from the group of anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias.

* * * * *